US010596244B2

(12) United States Patent
Roos et al.

(10) Patent No.: US 10,596,244 B2
(45) Date of Patent: Mar. 24, 2020

(54) PHARMACEUTICAL PREPARATION COMPRISING A COMBINATION OF STREPTOCOCCUS STRAINS AND LACTOBACILLUS STRAINS

(71) Applicant: ESSUM AB, Umea (SE)

(72) Inventors: Kristian Roos, Göteborg (SE); Eva Grahn Håkansson, Umeå (SE)

(73) Assignee: WINCLOVE HOLDING B.V., Amsterdam (NL)

( * ) Notice: Subject to any disclaimer, the term of this patent is extended or adjusted under 35 U.S.C. 154(b) by 0 days.

(21) Appl. No.: 14/878,743

(22) Filed: Oct. 8, 2015

(65) Prior Publication Data
US 2016/0089428 A1 Mar. 31, 2016

Related U.S. Application Data

(62) Division of application No. 12/998,615, filed as application No. PCT/SE2009/051300 on Nov. 17, 2009, now abandoned.

(60) Provisional application No. 61/115,283, filed on Nov. 17, 2008.

(30) Foreign Application Priority Data
Nov. 17, 2008 (SE) ........................ 0850079

(51) Int. Cl.
A61K 39/02 (2006.01)
A61K 39/085 (2006.01)
A61K 35/747 (2015.01)
C12R 1/225 (2006.01)
A61K 35/744 (2015.01)
C12N 1/20 (2006.01)
C12R 1/25 (2006.01)
C12R 1/46 (2006.01)
A23K 10/18 (2016.01)
A23K 50/10 (2016.01)
A61K 35/74 (2015.01)

(52) U.S. Cl.
CPC ............ A61K 39/085 (2013.01); A23K 10/18 (2016.05); A23K 50/10 (2016.05); A61K 35/74 (2013.01); A61K 35/744 (2013.01); A61K 35/747 (2013.01); C12N 1/20 (2013.01); C12R 1/225 (2013.01); C12R 1/25 (2013.01); C12R 1/46 (2013.01)

(58) Field of Classification Search
None
See application file for complete search history.

(56) References Cited

U.S. PATENT DOCUMENTS

| 5,322,686 A * | 6/1994 | Grahn ................. A23C 9/1236 424/93.44 |
| 6,479,051 B1 | 11/2002 | Bruce et al. |
| 6,761,885 B1 | 7/2004 | Hakansson et al. |
| 2005/0074440 A1* | 4/2005 | Lin ...................... A61K 35/747 424/93.45 |
| 2006/0258596 A1 | 11/2006 | Walsh et al. |
| 2008/0107634 A1 | 5/2008 | Mogna et al. |

FOREIGN PATENT DOCUMENTS

| EP | 1481681 A1 | 12/2004 | |
| WO | WO-9009186 A1 | 8/1990 | |
| WO | WO-1991009608 A1 | 7/1991 | |
| WO | WO199855131 * | 2/1998 | ............. A61K 35/74 |
| WO | WO-9855131 A1 | 12/1998 | |
| WO | WO-9907393 | 2/1999 | |
| WO | WO-9953932 A1 | 10/1999 | |
| WO | WO-2004030624 A2 | 4/2004 | |

(Continued)

OTHER PUBLICATIONS

Boyce et al. Journal of Clinical Microbiology, vol. 43, No. 12 pp. 5992-5995, 2005.*
Beighton et al. J.Med. Microbiol. vol. 35 pp. 367-372, Apr. 1991 (Year: 1991).*
Hatakka et al., "Effect of Long Term Consumption of Probiotic Milk on Infections in Children Attending Day Care Centres: Double Blind, Randomised Trial", 2001, BMJ, vol. 322, pp. 1-5, abstract.
Uehara et al., CID, vol. 32, May 15, 2001, pp. 1399-1407.

(Continued)

Primary Examiner — Gary B Nickol
Assistant Examiner — Khatol S Shahnan Shah
(74) Attorney, Agent, or Firm — Harness, Dickey & Pierce, P.L.C.

(57) ABSTRACT

A pharmaceutical preparation for prophylaxis against and treatment of Staphylococcus induced infections or conditions in humans and animals, is disclosed, wherein it comprises a combination of a) one or more viable α-Streptococcus strains chosen from the group consisting of the Streptococcus sanguis JI strains having the accession numbers NCTMB 40104, NCTMB 40105, NCIMB 40106, and NCIMB 40873, the Streptococcus mitis strains having the accession numbers NCIMB 40107, and NCIMB 40874, the Streptococcus oralis strains having the accession numbers NCIMB 40875 and NCIMB 40876, the Streptococcus lactis strain LIA having the accession number NCIMB 40157, and one or more variants thereof having the same or essentially similar effect; and b) one or more viable Lactobacillus strains chosen from the group consisting of the Lactobacillus rhamnosus strain LB2 I having the accession number NCIMB 40564, the Lactobacillus plantamm strain LB3 having the accession number DSM 17852, and the Lactobacillus plantarwn strain LB7 having the accession number DSM 1 7853, and one or more variants thereof having the same or essentially similar effect; in at least one pharmaceutically acceptable medium in which said strains maintain their viability, as well as a kit for and a method of prophylaxis and treatment of Staphylococcus induced infections and conditions, and use.

13 Claims, No Drawings

(56) References Cited

FOREIGN PATENT DOCUMENTS

| WO | WO-2006054135 A1 | 5/2006 |
| WO | WO-2007108763 A1 | 9/2007 |

OTHER PUBLICATIONS

International Search Report from PCT/SE2009/051300, dated Feb. 18, 2010.

Jain, Prashant K. et al., "Influence of Synbiotic Containing Lactobacillus Acidophilus La5, Bifidobacterium lactis Bb12, Streptococcus Thermophilus, Lactobacillus Bulgaricus and Oligofructor on Gut Barrier Function and Sepsis in Ciritically Ill Patients: A Randomized Controlled Trial," *Clinical Nutrition*, vol. 23, No. 4, Aug. 1, 2004, pp. 467-475.

Rolfe, Rial D., "The Role of Probiotic Cultures in the Control of Gastrointestinal Health," *The Journal of Nutrition*, Wistar Institute of Anatomy and Biology, vol. 130, No. 2, Supp. Jan. 1, 2000, pp. 396S-402S.

Roos, Kristian et al., "Effect of Recolonisation with 'Interfering' α Streptococci on Recurrences of Acute and Secretory Otitis Media in Children: Randomized Placebo Controled Trial," *BMJ*, vol. 322, Jan. 2001.

Roos, Krisian et al., "Alpha-Streptococci as Supplementary Treatment of Recurrent Streptococcal Tonsillitis: A Arandomized Placebo-Congrolled Study," *Scand. J. Infect. Dis.*, vol. 25, 1993, pp. 31-35.

Roos, Krisian et al., "Recolonization with Select a-Streptococci for Prophylaxis of Recurrent Streptococcal Pharyngotonsillitis—A Randomized Placebo-Controlled Multicentre Study," *Scand. J. Infect. Dis.*, vol. 28, 1996, pp. 459-462.

Falck, G. et al., "Tolerance and Efficacy of Interfering Alpha-streptococci in Recurrence of Streptococcal Pharyngotonsillitis: A Placebo-Controlled Study," *Acta Otolaryngol*, Stockholm, vol. 119, 1999, pp. 944-948.

\* cited by examiner

PHARMACEUTICAL PREPARATION COMPRISING A COMBINATION OF STREPTOCOCCUS STRAINS AND LACTOBACILLUS STRAINS

CROSS-REFERENCE TO RELATED APPLICATIONS

This application is a divisional of U.S. patent application Ser. No. 12/998,615, filed Jun. 20, 2011, which is a U.S. National Phase application of International Application No. PCT/SE2009/051300, filed on Nov. 17, 2009, which claims priority under 35 U.S.C. § 119(e), 120 and/or 365(c) to Swedish Application No. 0850079-5 filed on Nov. 17, 2008 and U.S. Provisional Application No. 61/115,283 filed on Nov. 17, 2008.

TECHNICAL FIELD

The present invention relates to a pharmaceutical preparation for prophylaxis against and treatment of *Staphylococcus* induced infections and conditions, to a kit therefor, to a method for prophylaxis against and treatment of *Staphylococcus* induced infections and conditions, and to uses of said pharmaceutical preparation or kit.

BACKGROUND OF THE INVENTION

*Staphylococcus* infections have since long been a widely spread problem around the world, which also gradually has been aggravated due to development of resistance against different antibiotic medicaments used for treatment of *Staphylococcus* infections.

*Staphylococci* are spherically formed Gram-positive bacteria that are common in our daily environment. Under a microscope they appear round and form in grape-like clusters. The *Staphylococcus* genus includes more than thirty species, e.g. *Staphylococcus aureus, Staphylococcus epidermidis*, and *Staphylococcus saprophyticus*. *Staphylococcus aureus* belongs to the normal human bacterial flora and is present on the skin, on mucous membranes, and in the nostrils (nares). *Staphylococcus epidermidis* is present on the skin, in the nostrils, and in the oral cavity, while *Staphylococcus saprophyticus* is present in the urinary tract.

*Staphylococcal* enterotoxins produced when these strains are allowed to grow in improperly stored food are a common cause of food poisoning leading to vomiting and diarrhoea.

*Staphylococcus epidermidis* is mostly present on the skin of humans and may induce infections with pus formation under the skin, in particular for persons with reduced immune resistance. These strains may also give rise to sepsis, in particular for severely diseased patients, e.g. having long term intravenous catheters.

*Staphylococcus saprophyticus* rarely induces diseases, but may in certain situations give rise to urinary tract infections.

In particular, *Staphylococcus aureus* gives rise to a wide variety of diseases in humans and animals through either toxin production or invasion. *Staphylococcus aureus, S. aureus* for short, also known as golden staph, is the most common cause of *Staphylococcus* infections, and can cause a range of illnesses from minor skin infections, such as pimples, impetigo, boils, cellulitis folliculitis, furuncles, carbuncles, scalded skin syndrome and abscesses, to life-threatening diseases, such as pneumonia, meningitis, osteomyelitis endocarditis, toxic shock syndrome (TSS), and septicemia. Its incidence is from skin, soft tissue, respiratory, bone, joint, and endovascular to wound infections. It is still one of the four most common causes of nosocomial infections, often causing post-surgical wound infections.

*S. aureus* may occur as a commensal on human skin, and in about a third of the population, it frequently also occurs in the nose, but in the throat less commonly. The occurrence of *S. aureus* under these circumstances does not always indicate infection and therefore does not always require treatment. It can survive on domesticated animals such as dogs, cats, pigs and horses. It can survive for some hours on dry environmental surfaces. *S. aureus* can infect other tissues when the normal barriers have been breached, e.g. skin or mucosal lining. This leads to furuncles (boils) and carbuncles (a collection of furuncles). In infants *S. aureus* infection can cause a severe disease called *Staphylococcal* scalded skin syndrome (SSSS). *S. aureus* infections can be spread through contact with pus from an infected wound, skin-to-skin contact with an infected person by producing hyaluronidase that destroy tissues, and contact with objects such as towels, sheets, clothing, or athletic equipment used by an infected person. Deeply situated *S. aureus* infections can be very severe. Prosthetic joints put a person at particular risk for septic arthritis, and *staphylococcal* endocarditis (infection of the heart valves) and pneumonia, which may be rapidly spread. *S. aureus* is extremely prevalent in atopic dermatitis patients, who are less resistant to it than other people. It often causes complications. The disease is most likely found in fertile active places of the human body, as well as the armpits, the hair and the scalp. Large pimples in those areas will, when popped, cause the worst of the infection. Some strains of *S. aureus* produce toxic shock syndrome toxin, which is the causative agent for toxic shock syndrome. Some *S. aureus* strains that produce an enterotoxin are the cause of *staphylococcal* food poisoning, as also mentioned above. Further, *S. aureus* is one of the causal agents of mastitis in dairy cows.

*Staphylococcus* strains have an extraordinary ability to develop resistance against antibiotics. *Staphylococcal* resistance to penicillin is mediated by penicillinase (a form of β-lactamase) production: an enzyme which breaks down the β-lactam ring of the penicillin molecule. Penicillinase-resistant penicillins such as methicillin, oxacillin, cloxacillin, dicloxacillin, and nafcillin, are able to resist degradation by *staphylococcal* penicillinase.

Today, *S. aureus* has become resistant to many commonly used antibiotics. In the UK, only 2% of all *S. aureus* isolates are sensitive to penicillin with a similar picture in the rest of the world, due to a penicillinase, which is a form of β-lactamase. The β-lactamase-resistant penicillins (methicillin, oxacillin, cloxacillin and flucloxacillin) were developed to treat penicillin-resistant *S. aureus* and are still used as first-line treatment. Methicillin was the first antibiotic in this class to be used. It was introduced in 1959, but only two years later the first case of methicillin-resistant *S. aureus* (in the following called MRSA for short) was reported in England.

Despite this, MRSA generally remained an uncommon finding even in hospital settings until the 1990s when there was an explosion in MRSA prevalence in hospitals, where it now is endemic.

MRSA infections in both the hospital and community setting are commonly treated with non-β-lactam antibiotics such as clindamycin (a lincosamine) and co-trimoxazole (also commonly known as trimethoprim/-sulfamethoxazole). Resistance to these antibiotics has also led to the use of new, broad-spectrum anti-Gram positive antibiotics such as linezolid because of its availability as an oral drug. First-line treatment for serious invasive infections due to MRSA currently include glycopeptide antibiotics (vancomycin and teicoplanin). There are a number of problems with these antibiotics, mainly centred around the need for intravenous administration (there is no oral preparation available), toxicity, and the need to regularly monitor drug levels by means of blood tests. There are also concerns that glycopeptide antibiotics do not penetrate very well into infected tissues. This is a particular concern with infections of the brain and meninges, and in endocarditis. Glycopeptides must not be used to treat methicillin-sensitive *S. aureus* as outcomes are inferior.

Because of the high level of resistance to penicillins, and because of the potential for MRSA to develop resistance to vancomycin, the Centers for Disease Control and Prevention have published guidelines for the appropriate use of vancomycin. In situations where the incidence of MRSA infections is known to be high, the attending physician may choose to use a glycopeptide antibiotic until the identity of the infecting organism is known. When the infection is confirmed to be due to a methicillin-susceptible strain of *S. aureus*, then treatment can be changed to flucloxacillin or even penicillin as appropriate. However, several newly discovered strains of MRSA show antibiotic resistance even to vancomycin and teicoplanin.

Vancomycin-resistant *S. aureus* (VRSA) is a strain of *S. aureus* that has become resistant to the glycopeptides. The first case of vancomycin-intermediate *S. aureus* (VISA) was reported in Japan in 1996, but the first case of *S. aureus* truly resistant to glycopeptide antibiotics was only reported in 2002. Three cases of VRSA infection have been reported in the United States as of 2005.

*Staphylococcus* infections, including MRSA, occur most frequently among the persons in hospitals and health care facilities. MRSA infections that occur in otherwise healthy people who have not been recently hospitalized or have not undergone any medical procedure are known as community-associated (CA)-MRSA-infections. The colonisation of MRSA can be long-resting, sometimes over years.

MRSA may colonize at different locations in the human body, such as in the ear, the nasal and the pharyngeal region, in the gastro-intestinal region, in the urine, and on the skin. Examples of skin infections are boils, abscesses, styes (infection of glands in the eyelid), carbuncles, cellulites, and impetigo. If colonized in the blood or in other organs or parts within the body, an infection occurs, e.g. septicaemia (blood poisoning), septic shock, septic arthritis, osteomyelitis, internal abscesses, meningitis, pneumonia, and endocarditis. Long-term carriers have a higher risk of infection and may also spread the MRSA to other people.

Prophylaxis against *Staphylococcus* infections is difficult, and vaccination is not a very effective way. Persons showing antibiotic resistance against *Staphylococcus* strains are normally isolated at an infection clinic or corresponding institute with a view to avoiding spread of infection. Thus, in particular MRSA has become a major problem in hospitals in many countries and the spread of MRSA has to be prevented.

As appears above, the treatment of MRSA depends on whether a person is infected with *Staphylococcus aureus* or only colonised. Most MRSA infections will require treatment in hospital and antibiotic treatment may need to continue for several weeks. If a person is colonised with MRSA and need to go into hospital for an operation, he requires treatment to remove the MRSA, e.g. with a special antibiotic cream on the skin or inside the nose to remove the bacteria. It may also be necessary to wash the skin and hair with an antiseptic shampoo and lotion. In the hospital a private room is also needed to stop MRSA spreading.

As appears above, there is a need of an improved treatment, and also prophylaxis, of *Staphylococcus* induced infections and also to prevent further spreading of *Staphylococci* from an individual carrying *Staphylococci*, regardless whether an infection has been developed or not, in particular in view of resistant *Staphylococcus* strains.

SUMMARY OF THE INVENTION

The object of the present invention is to reduce or eliminate the problems disclosed above in connection with *Staphylococcus* induced infections and conditions.

According to the present invention this object is achieved by a pharmaceutical preparation for prophylaxis against and treatment of *Staphylococcus* induced infections or conditions in humans and animals, wherein it comprises a combination of a) one or more viable α-*Streptococcus* strains chosen from the group consisting of the *Streptococcus sanguis* II strains having the accession numbers NCIMB 40104, NCIMB 40105, NCIMB 40106, and NCIMB 40873, the *Streptococcus mitis* strains having the accession numbers NCIMB 40107, and NCIMB 40874, the *Streptococcus oralis* strains having the accession numbers NCIMB 40875 and NCIMB 40876, the *Streptococcus lactis* strain L1A having the accession number NCIMB 40157, and one or more variants thereof having the same or essentially similar effect; and b) one or more viable *Lactobacillus* strains chosen from the group consisting of the *Lactobacillus rhamnosus* strain LB21 having the accession number NCIMB 40564, the *Lactobacillus plantarum* strain LB3 having the accession number DSM 17852, and the *Lactobacillus plantarum* strain LB7 having the accession number DSM 17853, and one or more variants thereof having the same or essentially similar effect;

in at least one pharmaceutically acceptable medium in which said strains maintain their viability.

Further, the present invention relates to a kit for prophylaxis against and treatment of *Staphylococcus* induced infections and conditions, wherein it comprises two or more separate formulations intended to be administered at the same time, or in sequence within a predetermined time period, to a human or an animal in need thereof, wherein said kit comprises the combination of a) and b) above and each formulation in the kit comprises at least one strain according to a) above and/or at least one strain according to b) above.

The present invention also relates to a method for prophylaxis against and/or treatment of a *Staphylococcus* induced infection or condition, wherein the pharmaceutical preparation or the kit according to the present invention is administered to a human or animal having need thereof.

In another aspect the present invention relates to use of the pharmaceutical preparation or the kit according to the present invention for the preparation of a medicament for prophylaxis against and/or treatment of *Staphylococcus* induced infections or conditions in humans and animals.

The pharmaceutical preparation or the kit according to the present invention may also be used for the preparation of a medicament for prophylaxis against and/or treatment of virus infections such as rhinovirus, coronavirus, parainfluenza virus, and adenovirus, in the upper respiratory tract.

A further disclosure of the objects, problems, solutions and features of the present invention will be apparent from the following detailed description of the invention including the experiments and with reference to the appended claims.

DETAILED DESCRIPTION OF PREFERRED EMBODIMENTS

The present inventors have surprisingly found that a new combination of different known micro-organism strains gives rise to an unforeseeable advantageous effect during prophylaxis against and treatment of *Staphylococcus* induced infections and conditions, i.e. it has an inhibitory, repressive, competitive and/or killing effect on *Staphylococcus* strains, e.g. *Staphylococcus aureus*, *Staphylococcus epidermidis*, and *Staphylococcus saprophyticus*. The combined strains originate from two main groups of microorganisms, more precisely α-*Streptococcus* strains, and *Lactobacillus* strains.

Neither of these two main groups of microorganisms has previously separately shown any similar good effect on *Staphylococci*, although LB21 has shown a slight beneficial effect on *Staphylococcus aureus* in general in the intestine during in vitro tests. The combination of these strains gives a surprising advantageous synergistic effect. Some of the *Streptococcus* strains in the pharmaceutical preparation according to the present invention are previously disclosed in WO 90/09186 (Essum AB). In this document these *Streptococcus* strains are disclosed to be useful in a pharmaceutical preparation for prophylaxis against and/or treatment of β-streptococcal tonsillitis. The *Streptococcus sanguis* II strains and the *Streptococcus mitis* strains in question were deposited with the National Collection of Industrial and Marine Bacteria Ltd (NCIMB), Torry Research Station, PO Box 31, 135 Abbey Road, Aberdeen AB9 8DG, Great Britain, on the 3 Feb. 1989, and have the accession numbers NCIMB 40104, NCIMB 40105, NCIMB 40106, and NCIMB 40107, respectively. Alternative names for these four strains are α89a, α502, α505, and α7213. The isolation, typing and medical function of these *Streptococcus* strains are disclosed in detail in WO 90/09186. The inhibiting effect of these α-*streptococcus* strains on the tonsillitis induced β-*streptococci* has been shown to depend in a high degree on the presence of bacteriocins produced by the α-*streptococci*.

A pharmaceutical preparation for prophylaxis and/or treatment of acute otitis media (inflammation of the ear) and middle otitis (inflammation of the middle ear) is disclosed in WO 99/53932 (Bacterum AB). Said preparation comprises some of the *Streptococcus* strains present in the combined pharmaceutical preparation according to the present invention, i.e. the micro-organism strains *Streptococcus sanguis* under the accession number NCIMB 40104, *Streptococcus sanguis* under the accession number NCIMB 40873, *Streptococcus oralis* under the accession number NCIMB 40875 (also called α4), *Streptococcus oralis* under the accession number NCIMB 40876 (also called α6) and *Streptococcus mitis* strains under the accession numbers NCIMB 40107, and NCIMB 40874, and optionally, other α-*Streptococcus* strains having essentially the same capacity, i.e. of inhibiting *Haemophilus influenzae*, *Streptococcus pneumoniae*, and *Moraxella catharralis*. The strains NCIMB 40873, 40874, 40875, and 40876 were deposited on 19 Mar. 1997 in National Collection of Industrial and Marine Bacteria Ltd (NCIMB), 23 St. Machar Drive, Aberdeen, AB2 1RY, Great Britain. The strain with the accession number NCIB 40104 was deposited on 3 Feb. 1989 (see WO 90/09186 above), and was thereafter designated NCIMB 40104. The isolation, typification and medical function of these strains are disclosed in detail in WO 99/53932.

See also Alpha-*streptococci* as supplementary treatment of recurrent *streptococcal* tonsillitis—a randomized placebo-controlled study. Roos K. Holm S E, Grahn E, Lind L. Scand J Infect Dis 25:31-35, 1993; Recolonization with selected alpha-streptococci for prophylaxis of recurrent *streptococcal* pharyngotonsillitis—a randomized placebo-controlled multicentre study. Roos K, Holm S E, Grahn E, Lagergren L. Scand J Infect Dis 28:459-462, 1996; The tolerance and efficacy of interfering alpha-sterptococci in recurrence of *streptococcal* pharyngitis—a placebo-controlled study. Falck G, Grahn Håkansson E, Holm S E, Roos K, Lagergren L. Acta Oto-Laryngologica, 119:944-948, 1999; and Effect of recolonisation with "interfering" alpha streptococci on recurrences of acute and secretory otitis media in children: randomised placebo controlled trial. Roos K, Grahn Håkansson E, Holm S E. BMJ, 322:210-212, 2001.

The α-*Streptococcus lactis* strain L1A is disclosed in WO 91/09608 and has the accession number NCIMB 40157. This strain was at the time classified as an α-*Streptococcus* strain being α-hemolytic, but has thereafter been re-classified as a *Lactococcus lactis* strain. Following the original classification, this strain is grouped under the *Streptococcus* strains a) in the combination according to the present invention.

A pharmaceutical preparation for prophylaxis against and/or treatment of gastrointestinal disorders in man and animals is disclosed in WO 98/55131 (Essum AB), wherein said preparation comprises a viable micro-organism strain in the form of the *Lactobacillus casei rhamnosus* strain LB21 with the accession number NCIMB 40564 and/or one or more variants thereof with an essentially similar function. The above-mentioned LB21 strain was deposited on 11 Jun. 1993 in National Collection of Industrial and Marine Bacteria Ltd (NCIMB), 23 St. Machar Drive, Aberdeen, AB2 1RY, Great Britain. The isolation, typing and medical function of this LB21 strain are disclosed in detail in WO 98/55131.

The *Lactobacillus casei rhamnosus* LB21, which is included here with the alternative term *Lactobacillus rhamnosus* LB21 in part b) of the combined pharmaceutical preparation according to the present invention, was isolated from faeces of infants and has proved to have a particularly pronounced inhibitory effect on the majority of the bacteria that are important to different types of intestinal infections in man, such as *Staphylococcus aureus* in general, but not MRSA, but substantially in view of different species such as *Salmonella, Shigella, Pseudomonas, Klebsiella-Enterobacter, Campylobacter, Clostridium difficile, Helicobacter pylori* etc. The strongly inhibitory effect of precisely LB21 on intestinally pathogenic bacteria is probably due to the fact that it produces specific acids but also a specific low-molecular protein or a specific low-molecular peptide, which is thermally stable, has a molecular weight below 5000 Daltons and which in a unique fashion has a detrimental effect on intestinally pathogenic bacteria.

The *Lactobacillus plantarum* strain LB3 having the accession number DSM 17852, and the *Lactobacillus plantarum* strain LB7 having the accession number DSM 17853, were deposited on Jan. 6, 2006, at Deutsche Sammlung von Mikroorganismen and Zellkulturen, Mascheroder Weg 1 b, D-38124 Braunschweig, and are also effective as *Lactobacillus* strains in the pharmaceutical preparation according to the present invention. Other *Lactobacillus* strains mentioned in the Examples below, e.g. LB45, LB64, LB66, LB87, LB99, LB931, and LB Ess-1, are also useful in the pharmaceutical preparation according to the present invention.

The LB45, LB64, LB66, LB87, and LB99 have not yet been deposited, but may be purchased from Essum AB, Box 3160, 903 04 Umeå, Sweden. The *Lactobacilus plantarum* strain LB931 has the accession number DSM11918, and the *Lactobacillus fermentum* strain LB Ess-1 has the accession number DSM17851. They have been deposited on 9 Jan. 1998 and on 6 Jan. 2006, respectively, at Deutsche Mascheroder Weg 1 b, D-38124 Braunschweig.

The unique combination of the bacterial strains in the pharmaceutical preparation according to the present invention exerts an advantageous synergistic effect in that, on the first hand, the *Streptococcus* strains occupies the epithelial cells, the matrix and the mucosal membranes and the skin creating a kind of physical barrier and prevents the staphylococci to attach to these cells. Thus, the bacterial flora on the afflicted part of the body is balanced and strengthened. On the other hand, the *Lactobacillus* strains according to the present invention produce substances that inhibit the growth of the *Staphylococci*, e.g. MRSA, but mainly strengthens the natural defence by modulating both the innate and the adaptive immune systems due to the structure of their bacteria cell walls and not due to metabolites produced by these *Lactobacillus* strains. A test on three blood donors, measured at mRNA level, shows that LB21 did not increase the INF-$\gamma$ levels or IL-4 levels of resting T cells, but on activated T cells the LB21 increases or decreases the cytokine response. Studies made in vivo by spraying the LB21 in the nose and thereafter sampling the nasopharyngeal fluid to measure the cytokines showed that IL-8 increased significantly after spray treatment. IL-8 is an important mediator of the immune reaction in the innate immune system response. The synergistic effect in vivo of special strains of $\alpha$-*streptococci* and *Lactobacilli* may depend on antimicrobial components e.g. bacteriocins from the $\alpha$-*streptococci* and their physical barrier on the mucous, together with the specific acids produced by the *Lactobacillus* strains and the stimulation of the immune system.

The combination of bacterial strains according to the present invention has shown good results in both in vitro and in vivo experiments with a view to reducing or eliminating harmful *Staphylococcus* strains on mucosal membranes and on the skin. Such good effects are not obtained if any one of the strains a) and b) according to the present invention is used only separately. Although the LB21 strain has shown an advantageous effect on only *Staphylococcus aureus* in general in the intestine during tests in vitro, the combination between LB21 and one or more of the *Streptococcus* strains in group a) gives a much improved effect in vitro. The combination has shown a good effect on all types of *Staphylococcus* strains, in particular *Staphylococcus aureus* strains, e.g. MRSA, i.e. methicillin-resistant *Staphylococcus aureus*, which is a huge worldwide problem.

According to the present invention, more than one strain from each of the groups a) and b) according to the present invention as defined in claim 1 may be used. In one embodiment, the *Streptococcus sanguis* strains $\alpha$89a, $\alpha$502, and $\alpha$505 are used as *Streptococcus* strains. In another embodiment, *Lactobacillus rhamnosus* LB21 and, optionally, one or more of the *Lactobacillus plantarum* strains LB3, LB7, and also LB931, are used in group b) as *Lactobacillus* strains. In another useful embodiment, the combination of *Streptococcus sanguis* $\alpha$89a and *Lactobacillus rhamnosus* LB21 is used. Other combinations of strains from group a) and b) are also effective.

Further, other *Streptococcus* strains and *Lactobacillus* strains having the same or essentially similar effect are also useful in the combination of strains in the pharmaceutical preparation according to the present invention. The expression "other *Streptococcus* strains and *Lactobacillus* strains having the same or essentially similar effect" used herein is intended to mean such strains which in combination in vivo eliminates or kills *Staphylococci*.

The best effect is obtained in vivo. In vitro, PBS filtrate results have shown that MRSA is completely killed within 6 h with a combination according to the present invention, more precisely with a combination of the strains $\alpha$89a and LB21.

During the same treatment conditions with only LB21, the MRSA is killed within 16 h, and with only $\alpha$-*Streptococci* the MRSA is not killed but only reduced as to the number.

The expression "*Staphylococcus* induced infections and conditions" is intended to mean an undesired propagation of *Staphylococcus* strains leading to an infection with painful swelling of tissues, as well as any other disease or infection by other micro-organism as a result of the *Staphylococcus* infection. This expression is also intended to include the condition where an individual has been colonised with *Staphylococci*, i.e. is a carrier of *Staphylococci*, e.g. a MRSA carrier, but has not yet developed an infection, i.e. does not suffer from any disease. However, such an individual has the ability to spread the *Staphylococci* to other individuals during a long period. Such individuals also are at high risk for developing MRSA infections. Pneumonia, soft-tissue infection, and central venous catheter infection are the most common infections. Examples of other infections and conditions are, as also stated above, minor skin infections, such as pimples, impetigo, boils, cellulitis folliculitis, furuncles, carbuncles, scalded skin syndrome, and abscesses, as well as life-threatening diseases, such as meningitis, osteomyelitis endocarditis, toxic shock syndrome (TSS), and septicemia.

The expression "prophylaxis against *Staphylococcus* induced infections and conditions" is intended to mean both prophylaxis for an individual, which not yet is a carrier of *Staphylococci*, and prophylaxis of an individual, which is a carrier of *Staphylococci*, from developing an infection or another *Staphylococcus* induced condition, but also to hinder the carrier to spread it to other persons.

The expression "ready-for-use preparation" used herein is intended to mean the final preparation to be administered to a human or an animal.

The expression "predetermined time period" used herein is intended to mean the maximum time period during which two or more different formulations in a kit can be administered while still maintaining an acceptable killing or inhibitory effect on *Staphylococcus* strains.

In one embodiment, the strains defined in group a) and the strains defined in group b) in the strain combination of the pharmaceutical preparation according to the present invention need necessarily not be present in the one and same preparation. Although the combination in the one and same preparation is more advantageous of several reasons, e.g. due to facilitated production and administration, the strains in group a) and the strains in group b) may be present in separate formulations and may be administered separately at the same time or within a predetermined time period. In such an embodiment, depending on how many different strains which are to be included in each of groups a) and b), respectively, the present invention constitutes a kit containing two or more different formulations, each containing at least one strain from group a) and/or at least one strain from group b). The kit may also contain one formulation containing two or more strains belonging to group a) or several formulations each containing one strain belonging to group a). The kit may also contain one formulation containing two or more strains belonging to group b) or several formulations each containing one strain belonging to group b). As to the synergistic action, said one or more formulations containing strains belonging to group a) and said one or more formulations containing strains belonging to group b) in the kit should be administered to the human or animal in need thereof within an as small time period as possible, preferably at the same time. A predetermined time period between said one or more formulations containing strains belonging to group a) and said one or more formulations containing strains belonging to group b) could be as long as 24 hours, more preferably 12 hours, and most preferably at the same time. The order of administration of such one or more formulations in a kit does not matter.

The pharmaceutical preparation or the kit according to the present invention may be intended for an oral, oromucosal, pharyngeal, nasal, dental, cutaneous/skin, vaginal, rectal, ear, or dialysis formulation. As stated above, the predetermined time period between administration of different formulations in the kit embodiment of the present invention may not be so long that the synergistic action not is obtained, e.g. due to non-optimal colonisation or undesired interaction with other strains, and is at most 24 hours, as stated above.

The pharmaceutically acceptable medium may be any medium conventionally used in the medical area, also containing conventionally used auxiliary agents and excipients, or may be a soured or fermented milk product, preferably sour milk, yoghurt and milk or fruit juice, ice-cream, soup and fruit drinks. The pharmaceutically acceptable medium may also be an NaCl solution, a glucose solution or skim milk, or be an animal feed stuff, preferably whey, dry fodder or a concentrated suspension, when administering the preparation according to the invention to animals. The strains in the pharmaceutical product and the kit according to the present invention may be present in a lyophilized form in the product ready for use.

For treatment of *Staphylococcus* induced infections or conditions in the oral cavity or the throat, the pharmaceutical preparation may be administered in the form of e.g. a spray, e.g. a pharyngeal spray or a buccal spray, a powder, a tablet, a cachet, a granule, a capsule, a suspension in a preferred medium, a mouth wash or a drink, syrup or solution.

For treatment of *Staphylococcus* induced infections and conditions on or in the skin, a pharmaceutical preparation in the form of a gel, a salve, an ointment, a foam, a paste, a lotion, an emulsion, a patch, a stick, a cream, e.g. a washing cream or an oil suspension, is administered.

For the treatment of *Staphylococcus* induced infections and conditions in the gasto-intestinal tract, the pharmaceutical preparation according to the present invention is administered in the form of a tablet, optionally with sustained release, a capsule, preferably enterocoated and/or colon-coated, a suspension, a solution, a drink, syrup, or a soup.

The pharmaceutical preparation according to the present invention has also surprisingly been shown to prevent virus induced infections and conditions in the upper respiratory tract, e.g. by such virus strains as rhinovirus, coronavirus, parainfluenza virus and adenovirus. More precisely, previous experiments performed with only the *Lactobacillus* strain LB21 have shown that among 130 children less virus infections arise in the upper respiratory tract and the intestine, compared to children who not were administered with LB21. The combination according to the present invention seems to further decrease the amount of virus infections. Thus, in one embodiment the *Lactobacillus* strain LB21 may be used for the production of a medicament for treatment of virus induced infections and conditions in the upper respiratory tract.

In another embodiment, a combination of the *Lactobacillus* strain LB21 and the α-*Streptococcus sanguis* II strain α89a may be used for the same purpose.

A clinical study on 54 children with SOM (secretory otitis media) that often had virus infection prior to the SOM has been made. The combination of LB21 and α89a was given as a nasal spray and 18 out of 37 (48%) children in the active group were much better or cured compared to 3 out of 17 (17%) in the placebo group.

The expression "virus induced infections and conditions" is intended to mean an undesired propagation of virus leading to an infection, such as common cold, sore throat, runny nose, nasal congestion, sneezing, and cough.

In the pharmaceutical preparation according to the present invention, alternatively the kit according to the present invention, said one or more *Streptococcus* strains is/are present in a total amount of $10^4$-$10^{11}$ cfu (colony-forming units)/ml, preferably $10^5$-$10^{10}$ cfu/ml, most preferably $10^6$-$10^9$ cfu/ml, of the ready-to-use preparation.

Accordingly, said one or more *Lactobacillus* strains is/are present in the pharmaceutical preparation, alternatively the kit, according to the present invention in a total amount of $10^4$-$10^{11}$ cfu (colony-forming unit)/ml, preferably $10^5$-$10^{10}$ cfu/ml, most preferably $10^6$-$10^9$ cfu/ml, of the ready-to-use preparation.

EXAMPLES

Example 1

In vitro Test
Production of a *Lactobacillus* PBS filtrate:
*Lactobacillus* LB21 was cultured in 5 ml MRS broth (37° C., 5% $CO_2$, 8 h). 1% (450 µl) LB21 culture was reinoculated in 6 tubes containing 45 ml fresh pre-heated MRS broth and was incubated at 37° C. and 5% $CO_2$ for 16 h. Thereafter the tubes were centrifuged at 3800 rpm at 20° C. for 20 min. The supernatants were discarded and the pellets were resuspended in 5 ml pre-heated PBS and incubated at 37° C. and 5% $CO_2$ for 5 h. Once an hour the tubes were gently mixed. After the incubation, the tubes were centrifuged at 3800 rpm at 8° C. for 20 min. All the supernatants were collected in a new tube, and the pH was measured (4.0-4.3) The supernatants were then sterile filtered through a 0.22 µm filter. The filtrates were stored in −20° C. in aliquots of 1 ml in 10 ml tubes until use.

Production of Control PBS Filtrate:

25 ml PBS solution was adjusted to a pH value of 4.3. The solution was there-after sterile filtered through a 0.22 μm filter and stored in −20° C. in aliquots of 1 ml in 10 ml tubes until use.

Interference Test:

Five different strains of MRSA (22, 26, 28, 29, and 33; isolated from MRSA colonised patients) were cultured in 5 ml TH broth at 37° C. for 6h. Thereafter, 1% (50 μl) of the MRSA culture was reinoculated in 5 ml fresh pre-heated TH broth and incubated in 37° C. for 17 h. The strains were then diluted in PBS and added to the LB21 PBS filtrates, to a mixture of LB21/*Streptococcus* (α89a) filtrate and to a control in PBS at a final concentration of $10^4$-$10^5$ cfu/ml. To all PBS filtrates, 5% TH broth was also added. The tubes were incubated at 37° C. and samples were taken after 0 and 24 h. The samples were cultured on tryptone soya agar plates and blood agar plates after appropriate dilutions. The LB21 supernatant alone inhibits the growth of all MRSA and also kill one of them (MRSA 29), while the combination of LB21 and α89a kills all of the tested MRSA within 24 hours, as appears from the column titled "Active sup" in the table. In the control group the MRSA grows to approximately $10^7$-$10^8$ cfu/ml.

Interference of LB21 supernatant, and a mix of LB21sup+α89a sup; pH 4.2

|  | 0 h CFU/ml | | 24 h CFU/ml | | | |
| --- | --- | --- | --- | --- | --- | --- |
|  | CFU at start | log | Control | log | Active sup | log |
| MRSA 22 in LB21 sup | 1.60E+04 | 4.20 | 2.42E+08 | 8.38 | 2.88E+03 | 3.46 |
| MRSA 26 in LB21 sup | 1.30E+04 | 4.11 | 1.26E+08 | 8.10 | 1.92E+03 | 3.28 |
| MRSA 28 in LB21 sup | 3.50E+03 | 3.54 | 3.28E+07 | 7.52 | 3.44E+03 | 3.54 |
| MRSA 29 in LB21 sup | 1.88E+04 | 4.27 | 2.53E+08 | 8.40 | 0.00E+00 | 0.00 |
| MRSA 33 in LB21 sup | 6.00E+02 | 2.78 | 1.17E+08 | 8.07 | 2.32E+03 | 3.37 |
| MRSA 22 in LB21/89a | 5.00E+03 | 3.70 | 8.64E+07 | 7.94 | 0.00E+00 | 0.00 |
| MRSA 26 in LB21/89a | 4.40E+03 | 3.64 | 5.28E+07 | 7.72 | 0.00E+00 | 0.00 |
| MRSA 28 in LB21/89a | 4.80E+03 | 3.68 | 2.72E+07 | 7.43 | 0.00E+00 | 0.00 |
| MRSA 29 in LB21/89a | 8.00E+02 | 2.90 | 8.40E+06 | 6.92 | 0.00E+00 | 0.00 |
| MRSA 33 in LB21/89a | 1.70E+03 | 3.23 | 1.02E+08 | 8.01 | 0.00E+00 | 0.00 |

In the table above, e.g. 1.60E+04 means $1.60 \times 10^4$, etc.

Example 2a

In vitro Test.

A combination of different *Lactobacillus* strains and an α-*Streptococci* mix of α89a, α502, α505, α4, and α6 was further tested in view of the capacity to inhibit and kill MRSA strains using the PBS supernatant method. At start the cfu was $2 \times 10^8$/ml of MRSA in the tubes. After 4, 6, 8, 10, 16 and 24 hours samples were taken. The results expressed in cfu/ml can be seen in the table below. The surprisingly better effect by the combination of *Lactobacillus* and α-*Streptococci* is due to a synergistic effect of the substances, e.g. specific acids and bakterocins, that are produced by the different strains. sup=supernatant

| PBS-sup | 0 h | 4 h | 6 h | 8 h | 10 h | 16 h | 24 h |
| --- | --- | --- | --- | --- | --- | --- | --- |
| LB21 | $2 \times 10^5$ | $1 \times 10^5$ | $6 \times 10^4$ | $1 \times 10^4$ | $5 \times 10^3$ | $1 \times 10^2$ | 0 |
| LB931 |  | $2 \times 10^5$ | $8 \times 10^4$ | $3 \times 10^4$ | $1 \times 10^4$ | $8 \times 10^3$ | $6 \times 10^3$ |
| LB45 |  | $1 \times 10^5$ | $5 \times 10^4$ | $1 \times 10^4$ | $6 \times 10^3$ | $2 \times 10^3$ | $6 \times 10^2$ |
| LB66 |  | $9 \times 10^4$ | $6 \times 10^4$ | $3 \times 10^4$ | $7 \times 10^3$ | $5 \times 10^2$ | $1 \times 10^2$ |
| LB99 |  | $1 \times 10^5$ | $5 \times 10^4$ | $1 \times 10^4$ | $5 \times 10^3$ | $1 \times 10^2$ | 0 |
| LB87 |  | $1 \times 10^5$ | $9 \times 10^4$ | $6 \times 10^4$ | $1 \times 10^4$ | $1 \times 10^3$ | $7 \times 10^2$ |
| LB64 |  | $1 \times 10^5$ | $7 \times 10^4$ | $1 \times 10^4$ | $6 \times 10^3$ | $1 \times 10^3$ | $3 \times 10^2$ |
| LB21 + alfa |  | $6 \times 10^2$ | 0 | 0 | 0 | 0 | 0 |
| LB931 + alfa |  | $3 \times 10^3$ | $1 \times 10^2$ | 0 | 0 | 0 | 0 |
| LB45 + alfa |  | $1 \times 10^3$ | $3 \times 10^2$ | 0 | 0 | 0 | 0 |
| LB66 + alfa |  | $8 \times 10^2$ | $9 \times 10^1$ | 0 | 0 | 0 | 0 |
| LB99 + alfa |  | $7 \times 10^2$ | $3 \times 10^1$ | 0 | 0 | 0 | 0 |
| LB87 + alfa |  | $6 \times 10^3$ | $1 \times 10^3$ | $2 \times 10^2$ | 0 | 0 | 0 |
| LB64 + alfa |  | $8 \times 10^3$ | $6 \times 10^2$ | $8 \times 10^1$ | 0 | 0 | 0 |

Example 2b

In vitro Test of Other Combinations

A further test was done according to Example 2a) but with new combinations of bacteria. Here LB931 and LB Ess-1 were tested in a combination with α89a and *Streptococcus lactis* L1A, and the concentration of remaining MRSA were measured after different time periods. The test strain was MRSA 22.

| PBS-sup | 4 h | 6 h | 10 h | 12 h | 24 h |
|---|---|---|---|---|---|
| LB Ess-1 | $1 \times 10^5$ | $5 \times 10^4$ | $2 \times 10^3$ | $6 \times 10^2$ | 0 |
| LB21 + 89a | $4 \times 10^3$ | $3 \times 10^1$ | 0 | 0 | 0 |
| LB931 + 89a | $3 \times 10^3$ | $2 \times 10^2$ | $4 \times 10^1$ | 0 | 0 |
| LBEss-1 + 89a | $2 \times 10^3$ | $6 \times 10^1$ | 0 | 0 | 0 |
| LB21 + L1A | $5 \times 10^2$ | 0 | 0 | 0 | 0 |
| LB931 + L1A | $6 \times 10^2$ | $9 \times 10^1$ | 0 | 0 | 0 |
| LBEss-1 + L1A | $1 \times 10^2$ | $4 \times 10^1$ | 0 | 0 | 0 |

Example 3

In vivo Test

To eliminate MRSA from the nose and the throat a suspension of *Lactobacillus* and α-*Streptococci* was used.

Eight persons colonised with MRSA since 2 to 5 years were sprayed with a suspension of *Lactobacilli* (LB21) and α-*Streptococci* (α89a, α505, α4) in their nose every morning. They also had to take 5 ml of the suspension in their mouth and then swallow it. This was done until two negative cultures were seen. Samples were taken from the patients and cultivated once a month for 4 months.

Results: All of the patients were negative for MRSA after 3 months of treatment. Five of the patients were negative already after 2 months.

| Patient | 1 month | 2 months | 3 months | 4 months |
|---|---|---|---|---|
| 1 | Pos | pos | neg | Neg |
| 2 | Pos | neg | neg | Neg |
| 3 | Pos | neg | neg | neg |
| 4 | Neg | neg | neg | neg |
| 5 | Pos | pos | neg | neg |
| 6 | Neg | neg | neg | neg |
| 7 | Pos | pos | neg | neg |
| 8 | Pos | neg | neg | neg |

Pos = Positive = Culture showing MRSA bacteria
Neg = Negative = No MRSA bacteria were found Example 4

In vivo test

To eliminate MRSA from the groin and the neck freeze dried bacteria of *Lactobacillus* LB21 mixed with α-Streptococci 89a were used.

Two persons colonised with MRSA on the skin, more precisely in the groin and on the neck, and in the nose were given a combination of LB21 and α89a in paraffin oil. They had to put the oil with the mixed freeze-dried powder on the skin every day for 8 weeks. They also sprayed the LB21/α89a mix in the nose using a bottle with spray equipment. The bacteria were freeze-dried in trehalose and dissolved in NaCl before use. Samples from the skin were taken every second week during the study time.

Results: The two MRSA colonised persons had negative MRSA cultures after 8 weeks of treatment, and already after four and six weeks of treatment negative cultures were found.

Results:

| Patient | 2 weeks | 4 weeks | 6 weeks | 8 weeks |
|---|---|---|---|---|
| 1 nose | pos | pos | neg | neg |
| 1 skin | pos | neg | pos | neg |
| 2 nose | pos | neg | neg | neg |
| 2 skin | pos | neg | neg | neg |

Example 5

Clinical Test in vivo

A young boy, the only person in a family that had stayed positive after the standard treatment with Descutan and Bactoban, were given a combination of LB21 and α89a as a spray in the nose and as a mouthwash in the throat. After one month he became MRSA negative in the nose (4 negative samples), and after 4 months he was MRSA negative (two negative samples) in the throat.

The invention claimed is:

1. A method for the treatment of a multi-resistant *Staphylococcus aureus* (MRSA) induced infection or condition, wherein the MRSA induced infection or condition is present in/on at least one selected from a nasal region and a pharyngeal region, the method comprising:
   administering, to a human or animal that is an MRSA carrier, a combination of
      a) one or more viable α-*Streptococcus* strains chosen from the group consisting of *Streptococcus sanguis* II strains having the accession numbers NCIMB 40104, and NCIMB 40106, and *Streptococcus mitis* strains having the accession number NCIMB 40874, and
      b) *Lactobacillus rhamnosus* strain LB21 having the accession number NCIMB 40564;
   wherein the combination further includes at least one pharmaceutically acceptable medium.

2. The method of claim 1, wherein the combination is administered as one selected from an oral, oromucosal, and nasal formulation.

3. The method of claim 1, wherein the combination is in the form of one selected from an oil suspension, a spray, a suspension, a solution, an emulsion, a nasal spray, and a buccal spray.

4. The method of claim 1, wherein the at least one pharmaceutically acceptable medium is at least one selected from a soured milk product, a fermented milk product and combinations thereof.

5. The method of claim 1, further comprising:
   lyophilizing the one or more viable α-*Streptococcus* strains and the one or more viable *Lactobacillus strains*, prior to the administering of the combination.

6. The method of claim 5, wherein the combination is present in one selected from a NaCl solution, a glucose solution, and skim milk.

7. The method of claim 1, wherein the combination includes $10^4$-$10^{11}$ colony-forming units per ml of a ready-to-use preparation of the one or more viable α-*Streptococcus* strains.

8. The method of claim 7, wherein the combination includes $10^6$-$10^9$ colony-forming units per ml of a ready-to-use preparation of the one or more viable α-*Streptococcus* strains.

9. The method of claim 1, wherein the combination includes $10^4$-$10^{11}$ colony-forming units per ml of a ready-to-use preparation of the one or more viable *Lactobacillus* strains.

10. The method of claim 9, wherein the combination includes $10^6$-$10^9$ colony-forming units per ml of a ready-to-use preparation of the one or more viable *Lactobacillus* strains.

11. The method of claim 1, wherein the administering the combination includes administering at least two separate formulations at the same time, or in sequence, to the human or animal, each of the at least two separate formulations including at least one strain selected from the one or more viable α-*Streptococcus* strains, the one or more viable *Lactobacillus* strains, and a combination thereof.

12. The method of claim 11, wherein the at least two separate formulations are administered to the human or animal in sequence within a time period of 24 hours.

13. The method of claim 11, wherein the at least two separate formulations are administered to the human or animal at the same time.

\* \* \* \* \*